(12) United States Patent
Tae et al.

(10) Patent No.: US 8,486,528 B2
(45) Date of Patent: Jul. 16, 2013

(54) TEMPERATURE-SENSITIVE NANO-CARRIERS

(75) Inventors: Gi-yoong Tae, Gwangju (KR); Won-il Choi, Pyeongchang-gun (KR); Ja-young Kim, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 844 days.

(21) Appl. No.: 12/355,299

(22) Filed: Jan. 16, 2009

(65) Prior Publication Data

US 2009/0196937 A1    Aug. 6, 2009

(30) Foreign Application Priority Data

Jan. 22, 2008  (KR) .................. 10-2008-0006848
Aug. 12, 2008  (KR) .................. 10-2008-0079136

(51) Int. Cl.
*A61K 9/14*  (2006.01)
(52) U.S. Cl.
USPC ............ 428/402; 424/489; 424/501; 428/357
(58) Field of Classification Search
USPC ........................... 428/357, 402; 424/489, 501
See application file for complete search history.

(56) References Cited

U.S. PATENT DOCUMENTS 7,226,617 B2 *  6/2007  Ding et al. .................... 424/486

FOREIGN PATENT DOCUMENTS

KR    100868724 B1   11/2008

OTHER PUBLICATIONS

Choi et al., "One pot, single phase synthesis of thermo-sensitive nano-carriers by photo-crosslinking of a diacrylated pluronic." J. Mater. Chem., 2008, 18, 2769-2774.

* cited by examiner

*Primary Examiner* — Ana Woodward
(74) *Attorney, Agent, or Firm* — Rothwell, Figg, Ernst & Manbeck, P.C.

(57) ABSTRACT

The present invention relates to a process of preparing a biocompatible temperature-sensitive nano-carrier, which comprises the steps of (a) preparing a polymer dispersion comprising a water-soluble biocompatible polymer with photo-crosslinkable functional group(s), (b) preparing a polymer-initiator solution by adding an initiator to the polymer dispersion, and (c) preparing the nano-carrier by irradiating light onto the polymer-initiator solution, wherein the average diameter of the nano-carrier changes depending on temperature, and also relates to a temperature-sensitive nano-carrier. Nano-carriers of the present invention are temperature-sensitive, and their average diameter and pore size reversibly change in response to temperature change. In an embodiment of the present invention, nano-carriers can be prepared via a one-pot single-phase synthesis. A process of the present invention overcomes the conventional problems such as the use of organic solvent, complicated preparation steps, a relatively high manufacture cost and a low loading efficiency. Moreover, a process of the present invention can ensure the stability of drugs without necessitating high-speed homogenization or ultrasonification generally carried out in the conventional process.

6 Claims, 8 Drawing Sheets

| Copolymer | MW[a] | Average no. of EO units (x)[b] | Average no. of PO units (y)[b] | HLB[c] |
|---|---|---|---|---|
| F68 | 8400 | 152.73 | 28.97 | 29 |
| F127 | 12600 | 200.45 | 65.17 | 22 |

100
TEMPERATURE-SENSITIVE NANO-CARRIERS

CROSS REFERENCE TO RELATED APPLICATIONS

This application claims priority from Korean patent application No. 10-2008-0006848 filed on Jan. 22, 2008, and Korean patent application No. 10-2008-0079136 filed on Aug. 12, 2008, all of which are incorporated herein by reference in their entireties for all purposes.

BACKGROUND (a) Technical Field

The present invention relates to temperature-sensitive nano-carriers.

(b) Background Art

Nanoparticle systems for delivering therapeutic proteins or drugs are generally synthesized by emulsion evaporation using organic solvents. However, these conventional methods need to include complicated steps, and also have problems associated with the use of organic solvents such as cytotoxicity and an increasing preparation cost (T. G. Park, et al., *Biomacromolecules* 8 (2007) 650-656; T. G. Park, et al., *Biomacromolecules* 7 (2006) 1864-1870; D. T. Birnbaum, et al., *J. Control. Rel.* 65 (2000) 375-387). For these reasons, there have been extensive researches exerted to develop a novel method of preparing nanoparticles that can ensure the stability of drugs encapsulated inside nanoparticles.

To overcome these problems, there have been attempts to use supercritical fluids, which are nontoxic solvents, for the preparation of nanoparticles. However, this process is not widely employed because most polymers exhibit a limited solubility in supercritical fluids (K. S. Soppimath et al., *J. Control. Rel.* 70 (2001) 1-20).

U.S. Pat. No. 5,019,400 discloses a process of preparing microspheres for protein drug delivery by spraying a biocompatible polymer, poly(D,L-lactic acid-co-glycolic acid) (referred to as 'PLGA' hereinafter), into cold liquid. However, organic solvent was used for dissolving PLGA, and the hydrophobicity of the organic solvent used for dissolving PLGA causes various problems.

U.S. Pat. No. 6,586,011 discloses a process of preparing a nanoparticle system for protein delivery by means of spraying into a cold liquid. However, a crosslinking agent used for manufacturing nanoparticles seriously damages the stability of the protein drugs.

A solvent evaporation method used for preparing nanoparticles also generates various problems associated with the use of organic solvent. Meanwhile, a salting-out method has been developed as an attempt to use a water-miscible organic solvent (e.g., acetone) instead of highly hydrophobic and toxic organic solvent for preparing poly(D,L-lactic acid) (referred to as 'PLA' hereinafter) nanoparticles (E. et al., *Pharm. Res.* 10 (1993) 1732-1737). However, this method still has problems such as a lowered activity and stability of protein drugs.

The information disclosed in the above Background section is only for the enhancement of understanding of the background of the invention and therefore it may contain information that does not form the prior art that is already known in this country to a person of ordinary skill in the art.

All publications, patents and patent applications cited herein, whether supra or infra, are hereby incorporated by reference in their entirety to the same extent as if each individual publication, patent or patent application was specifically and individually indicated to be incorporated by reference.

SUMMARY OF THE DISCLOSURE

The present inventors have extensive researches to develop an efficient process of preparing drug delivery system, and finally achieved a simple single-phase process of preparing superior thermo-sensitive nano-carriers comprising the step of crosslinking a water-soluble biocompatible polymer having a photo-crosslinkable functional group under appropriate conditions, thereby completing the present invention. The present invention has been made in an effort to solve the above-described problems associated with prior art.

In an aspect, the present invention provides a process of preparing biocompatible temperature-sensitive nano-carriers.

In another aspect, the present invention provides a process of preparing a sustained-release drug delivery system.

In still another aspect, the present invention provides temperature-sensitive sustained-released nano-carriers.

The above and other features of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
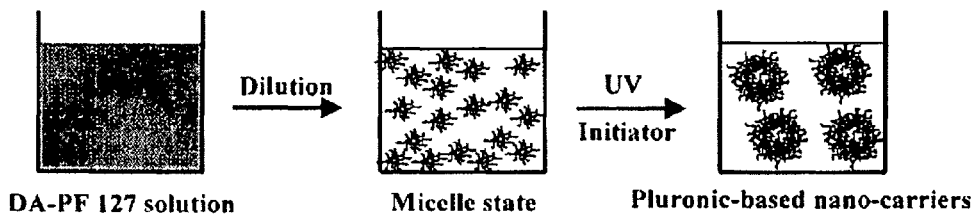
FIG. 1 schematically represents the preparation of pluronic-based nano-carriers by single phase photo-polymerization.
Figure 1:
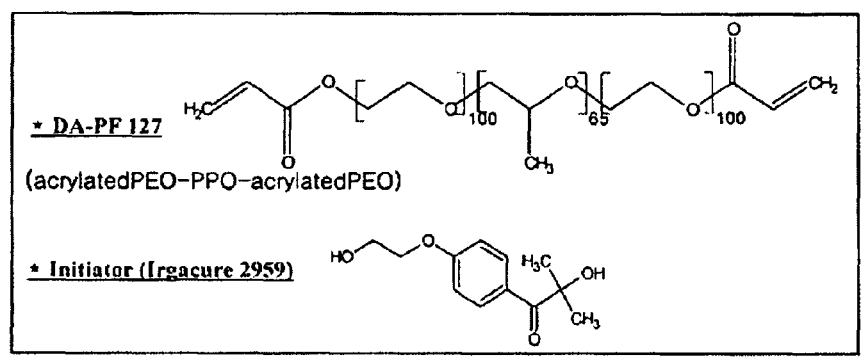

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

DETAILED DESCRIPTION

Reference will now be made in detail to the preferred embodiments of the present invention, examples of which are illustrated in the drawings attached hereinafter, wherein like reference numerals refer to like elements throughout. The embodiments are described below so as to explain the present invention by referring to the figures.

In an aspect, the present invention provides a process of biocompatible temperature-sensitive nano-carriers, which comprises the steps of (a) preparing a polymer dispersion comprising a water-soluble biocompatible polymer with photo-crosslinkable functional group(s); (b) preparing a polymer-initiator solution by adding an initiator to the polymer dispersion; and (c) preparing the nano-carriers by irradiating light onto the polymer-initiator solution; wherein the average diameter of the nano-carriers changes depending on temperature.

The present inventors have extensive researches to develop an efficient process of preparing drug delivery system, and finally achieved a simple single-phase process of preparing superior thermo-sensitive nano-carriers comprising the step of crosslinking a water-soluble biocompatible polymer having a photo-crosslinkable functional group under appropriate conditions, thereby completing the present invention. The present invention has been made in an effort to solve the above-described problems associated with prior art.

As used herein, the term of 'a biocompatible polymer' refers to a polymer having the tissue compatibility and the blood compatibility so that it causes neither the tissue necrosis nor the blood coagulation upon contact with tissue or blood.

As used herein, the term of 'a water-soluble biocompatible polymer' means a biocompatible polymer soluble in water or water-miscible solvent (e.g., methanol, ethanol, acetone, acetonitrile, N,N-dimethylformamide and dimethylsulfoxide), preferably in water.

Preferred examples of a water-soluble biocompatible polymer herein include but are not limited to poly(ethylene glycol), poly(ethylene oxide), poly(vinyl alcohol), poly(ethylene oxide)-poly(propylene oxide) block copolymer, alkylcellulose, hydroxyalkylcellulose, heparin, hyaluronic acid, chitosan, dextran and alginate. When a surfactant-like polymer comprising hydrophobic and hydrophilic parts is used among the water-soluble biocompatible polymer, it is preferred to additionally introduce hydrophobic parts to this polymer for achieving the aims of the present invention.

More preferably, a water-soluble biocompatible polymer herein is a poloxamer-based polymer. Most preferably, a water-soluble biocompatible polymer herein is a polymer of Formula 1:

  Formula 1 wherein PE is ethylene oxide; PPO is propylene oxide; each of PC1 and PC2 is a photo-crosslinkable functional group; and each of x, y and z is independently an integer of 1-10,000.

A photo-crosslinkable functional group is preferred to exist at the end of a biocompatible polymer.

In a preferred embodiment, a photo-crosslinkable functional group comprises a C=C double bond. Preferable examples of a photo-crosslinkable functional group include but are not limited to acrylate, diacrylate, oligoacrylate, methacrylate, dimethacrylate, oligomethacrylate, coumarin, thymine and cinnamate, more preferably acrylate, diacrylate, oligoacrylate, methacrylate, dimethacrylate and oligomethacrylate, most preferably acrylate.

Although any conventional initiators can be used in the present invention without limitation, a preferred type of initiator is a radical photoinitiator that undergoes a photoreaction under absorption of UV or visible and produces reactive species, thereby initiating the polymerization. Examples of a photoinitiator herein include but are not limited to ethyl eosin, 2,2-dimethoxy-2-phenyl acetophenone, 2-methoxy-2-phenylacetophenone, 2-hydroxy-1-[4-(2-hydroxyethoxy)phenyl]-2-methyl-1-propanone (Irgacure 2959 or Darocur 2959), camphorquinone, acetophenone, acetophenone benzyl ketal, 1-hydroxycyclohexy phenyl ketone, 2,2-dimethoxy-2-phenylacetophenone, xanthone, fluorenone, benzaldehyde, fluorene, anthraquinone, triphenylamine, carbazole, 3-methylacetophenone, 4-chlorobenzophenone, 4,4'-dimethoxybenzophenone, 4,4'-diaminobenzophenone, benzoin propyl ether, benzoin ethylether, benzyl dimethyl ketal, 1-(4-isopropylphenyl)-2-hydroxy-2-methylpropan-1-one, 2-hydroxy-2-methyl-1-phenylpropan-1-one, thioxanthone, diethylthioxanthone, 2-isopropylthioxanthone, 2-chlorothiothioxanthone, 2-methyl-1-[4-(methylthio)phenyl]-2-morpholino-propan-1-one, 2,4,6-trimethylbenzoyl diphenylphosphine oxide and bis-(2,6-dimethoxybenzoyl)-2,4,4-trimethylpentylphosphine oxide.

Irgacure 2959, a photoinitiator used in an embodiment below, is known as almost non-cytotoxic (Kristi S. Anseth, et al., Cytocompatibility of UV and visible light photoinitiating systems on cultured NIH/3T3 fibroblasts in vitro. *J. Biomater. Sci. Polymer Edn.*, 2000. 11(5): P. 439-457).

In the step (c), nano-carriers are prepared by irradiating visible or UV onto a solution comprising a photoinitiator and a photo-crosslinkable polymer, thereby crosslinking the polymer. UV is preferred for the crosslinking. In an embodiment, a UV lamp for a thin layer chromatography can be used for irradiating UV light for its relatively lower price and better availability. This UV lamp is also appropriate for an initiator that is decomposed to generate radicals by the radiation of 365 nm UV (e.g., Irgacure 2959).

In a preferred embodiment, a process herein further comprises the step (d) of functionalizing nano-carriers with a biocompatible/biofunctional polymer that is of a different kind from the polymer used in the step (a). In this case, examples of biocompatible/biofunctional polymers include but are not limited to heparin, alginate, hyaluronic acid, chitosan, chondroitin sulfate, dermatan 5-sulfate, keratan sulfate, dextran sulfate, poly(ethylene imine) and polylysine. Among these polymers, heparin is an anionic polysaccharide approved by FDA as non-cytotoxic.

In a preferred embodiment, the steps (a)-(c) are carried out in an aqueous dispersion phase without using an organic dispersion phase, i.e. in a single phase. More specifically, nano-carriers can be prepared by irradiating light onto an aqueous dispersion comprising a biocompatible polymer and an initiator. Moreover, the synthesis of the present invention is carried out via a one-pot reaction. In this respect, a process of the present invention can be referred to as a one-pot single-phase synthesis.

In a preferred embodiment, the average diameter of temperature-sensitive nano-carriers herein increases as temperature decreases, whereas the average diameter decreases as temperature increases. In a more preferred embodiment, the average diameter of nano-carriers measured at 4° C. is 3-20 times, more preferably 4-15 times, still more preferably 5-12 times, most preferably 7-10 times, higher than that measured at 40° C. The modulation of average diameter of nano-carriers herein is reversible in response to temperature change.

A pore size in nano-carriers changes depending on the diameter of the nano-carriers. After drugs to be delivered are encapsulated inside enlarged pores of nano-carriers at a lower temperature, for example 4° C., the administration of the nano-carriers into a human body decreases the pore size, thereby enabling the sustained release of the drugs.

In a preferred embodiment, temperature-sensitive nano-carriers herein have a pore size of 3-20 nm, more preferably 3-15 nm, most preferably 5-10 nm when measured at 37° C.

In a preferred embodiment, temperature-sensitive nano-carriers are nanoparticulate without leading to a hydrogel state. As ascertained in Examples herein, nano-carriers herein are round-shaped nanoparticles. In a preferred embodiment, nano-carriers have an average diameter of 50-500 nm, more preferably 100-400 nm, most preferably 120-300 nm. In another preferred embodiment, nanoparticles herein are preferred to have an average diameter of 400 nm or less so that the sterilization of the final nano-carriers may be conveniently conducted by using a sterile filter. Nano-carriers herein are preferred to have a polydispersity of 0.1 or less because a polydispersity of 0.1 or less is considered as a stable monodispersity. More preferably, nano-carriers herein have a polydispersity of 0.01-0.1.

In a preferred embodiment, a targeting ligand is bound on the surface of nano-carriers herein. Examples of a targeting ligand herein include without limitation a hormone, an antibody, a cell-adhesion molecules, a saccharide and a neurotransmitter.

A process of the present invention overcomes the conventional problems such as the use of organic solvent, complicated preparation steps, a relatively high manufacture cost and a low loading efficiency. Moreover, a process of the present invention can ensure the stability of therapeutic agents by avoiding denaturation or aggregation of the agents without necessitating high-speed homogenization or ultrasonification generally carried out in the conventional process.

In another aspect, the present invention provides a process of preparing a sustained-release drug delivery system, which comprises the steps of (a) preparing a mixture by mixing temperature-sensitive nano-carriers comprising a temperature-sensitive biocompatible polymer with a material to be delivered, and (b) incubating the mixture, thereby allowing the material to be delivered to be spontaneously encapsulated inside the nano-carrier.

The aforedescribed process of preparing temperature-sensitive nano-carriers can be applied to the preparation of a sustained-release drug delivery system herein. Description in common is omitted here for avoiding complications.

In a preferred embodiment, a water-soluble biocompatible polymer herein is a polymer of Formula 1:

 Formula 1 wherein PE is ethylene oxide; PPO is propylene oxide; each of PC1 and PC2 is a photo-crosslinkable functional group; and each of x, y and z is independently an integer of 1-10,000.

In a preferred embodiment, a photo-crosslinkable functional group comprises a C=C double bond. Preferable examples of a photo-crosslinkable functional group include but are not limited to acrylate, diacrylate, oligoacrylate, methacrylate, dimethacrylate, oligomethacrylate, coumarin, thymine and cinnamate.

In a preferred embodiment, the average diameter of temperature-sensitive nano-carriers herein increases as temperature decreases.

In a preferred embodiment, temperature-sensitive nano-carriers are not hydrogel but nanoparticulate. In a preferred embodiment, temperature-sensitive nano-carriers herein have a pore size of 3-20 nm when measured at 37° C.

In a preferred embodiment, temperature-sensitive nano-carriers herein are crosslinked.

Various therapeutically effective materials can be delivered by a sustained-release drug delivery system of the present invention without limitation. In a preferred embodiment, examples of a material to be delivered in the present invention include but are not limited to a protein, a nucleic acid, a nanoparticle and a fluorescent material.

Examples of a protein that can be delivered by a drug delivery system herein include but are not limited to a hormone, a hormone analog, an enzyme, an enzyme inhibitor, a signaling protein or segments thereof, an antibody or segments thereof, a single-chain antibody, a binding protein or a binding domain thereof, an antigen, an attachment protein, a structural protein, a regulatory protein, parasporal protein, a cytokine, a transcription factor, a blood clotting factor and a vaccine. Specific examples of a protein that can be delivered by a drug delivery system herein include, without limitation, insulin, IGF-1 (insulin-like growth factor 1), a growth hormone, erythropoietin, G-CSFs (granulocyte-colony stimulating factors), GM-CSFs (granulocyte/macrophage-colony stimulating factors), interferon alpha, interferon beta, interferon gamma, interleukin-1 alpha and beta, interleukin-3, interleukin-4, interleukin-6, interleukin-2, EGFs (epidermal growth factors), calcitonin, VEGF (vascular endothelial cell growth factor), FGF (fibroblast growth factor), PDGF (platelet-derived growth factor), ACTH (adrenocorticotropic hormone), TGF-β (transforming growth factor beta), BMP (bone morphogenetic protein), TNF (tumor necrosis factor), atobisban, buserelin, cetrorelix, deslorelin, desmopressin, dynorphin A (1-13), elcatonin, eleidosin, eptifibatide, GHRH-II (growth hormone releasing hormone-II, gonadorelin, goserelin, histrelin, leuprorelin, lypressin, octreotide, oxytocin, pitressin, secretin, sincalide, terlipressin, thymopentin, thymosine al, triptorelin, bivalirudin, carbetocin, cyclosporine, exedine, lanreotide, LHRH (luteinizing hormone-releasing hormone), nafarelin, parathormone, pramlintide, T-20 (enfuvirtide), thymalfasin and ziconotide.

Examples of a nucleic acid that can be delivered by a sustained-release drug delivery system herein include, without limitation, a DNA, a DNA aptamer, an RNA aptamer, an antisense oligonucleotide, siRNA, shRNA, a plasmid and a vector.

Examples of a nanoparticle that can be delivered by a sustained-release drug delivery system herein include, without limitation, gold nanoparticles, silver nanoparticles, iron nanoparticles, transition metal nanoparticles and metal oxide nanoparticles (e.g., ferrite nanoparticles). Ferrite nanoparticles delivered by a drug delivery system herein can be used as an imaging agent for MR (magnetic resonance).

A fluorescent material to be delivered by a sustained-release drug delivery system herein is preferred to be bound to a carrier such as a protein or metal nanoparticles (e.g., magnetic nanoparticles). Examples of a fluorescent material herein include but are not limited to fluorescein and derivatives thereof, rhodamine and derivatives thereof, Lucifer Yellow, B-phycoerythrin, 9-acridine isothiocyanate, Lucifer Yellow Vs, 4-acetamido-4'-isothio-cyanatostilbene-2,2'-disulfonic acid, 7-diethylamino-3-(4'-isothiocyanatophenyl)-4-methylcoumarin, succinimidyl-pyrene butyrate, 4-acetamido-4'-isothiocyanatostilbene-2,2'-disulfonic acid derivative, LC™-Red 640, LC™-Red 705, Cy5, Cy5.5, lysamine, isothiocyanate, erythrosin isothiocyanate, diethylenetriamine pentacetate, 1-dimethylaminonaphthyl-5-sulfonate, 1-anilino-8-naphthalene sulfonate, 2-p-touidinyl-6-naphthalene sulfonate, 3-phenyl-7-isocyanatocoumarin, 9-isothiocyanatoacridine, acridine orange, N-(p-(2-benzoxazolyl)phenyl)maleimide, benzoxadiazole, stilbene and pyrene.

In an embodiment of the present invention, one of the features is that a material to be delivered can be spontaneously encapsulated inside nano-carriers simply by mixing the nano-carriers and the material to be delivered. That is, a material to be delivered can be spontaneously loaded on nano-carriers by a mere close contact of nano-carriers and the materials to be delivered in the absence of further treatment.

In a preferred embodiment, drugs are encapsulated inside nano-carriers in an aqueous dispersion phase without using an organic dispersion phase.

In a preferred embodiment, the encapsulation is carried out at 0-20° C., more preferably 4-10° C., most preferably 4-6° C.

The aforementioned spontaneous encapsulation in aqueous solution can remarkably increase the stability of therapeutic agents, particularly protein drugs. Encapsulation efficiency is as high as 90% or higher in the spontaneous encapsulation inside a drug delivery system herein. Moreover, a process of the present invention neither uses organic solvents during the drug loading step nor necessitates high-speed homogenization or ultrasonification generally carried out in the conventional process, thereby enabling to ensure the stability of therapeutic agents by avoiding denaturation or aggregation of the agents.

In a still another aspect, the present invention provides temperature-sensitive sustained-released nano-carriers comprising a water-soluble biocompatible polymer crosslinked through a photo-crosslinkable functional group at the end of the polymer, wherein the average diameter of the polymer changes depending on temperature, and the polymer has a nanoparticulate form.

The description above can be applied to sustained-release drug delivery system of the present invention. Description in common is omitted here for avoiding complications.

In a preferred embodiment, a photo-crosslinkable functional group comprises a C=C double bond. Preferable examples of a photo-crosslinkable functional group include but are not limited to acrylate, diacrylate, oligoacrylate, methacrylate, dimethacrylate, oligomethacrylate, coumarin, thymine and cinnamate.

Preferred examples of a water-soluble biocompatible polymer herein include but are not limited to poly(ethylene glycol), poly(ethylene oxide), poly(vinyl alcohol), poly(ethylene oxide)-poly(propylene oxide) block copolymer, alkylcellulose, hydroxyalkylcellulose, heparin, hyaluronic acid, chitosan, dextran and alginate.

More preferably, a water-soluble biocompatible polymer herein is a polymer of Formula 1:

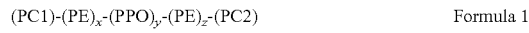

(PC1)-(PE)$_x$-(PPO)$_y$-(PE)$_z$-(PC2)     Formula 1 wherein PE is ethylene oxide; PPO is propylene oxide; each of PC1 and PC2 is a photo-crosslinkable functional group; and each of x, y and z is independently an integer of 1-10,000.

In a preferred embodiment, the average diameter of temperature-sensitive nano-carriers herein increases as temperature decreases.

In a preferred embodiment, nano-carriers herein are dispersed in an aqueous dispersion phase. In a preferred embodiment, nano-carriers herein have a pore size of 3-20 nm when measured at 37° C.

In a preferred embodiment, nano-carriers herein are functionalized with a different kind of biocompatible polymer.

In a preferred embodiment, nano-carriers herein comprise protein, nucleic acid, nanoparticle or fluorescent material.

In a preferred embodiment, a targeting ligand is bound on the surface of nano-carriers herein. Examples of a targeting ligand herein include without limitation a hormone, an antibody, a cell-adhesion molecules, a saccharide and a neurotransmitter.

Representative features and advantages of the present invention can be summarized as follows:

(i) Nano-carriers of the present invention are temperature-sensitive, and their average diameter and pore size reversibly change in response to temperature change;

(ii) In an embodiment of the present invention, nano-carriers can be prepared via a one-pot single-phase synthesis;

(iii) In an embodiment of the present invention, a material to be delivered can be spontaneously encapsulated inside nano-carriers;

(iv) Nano-carriers of the present invention can be used as a sustained-release drug delivery system because the pores of nano-carriers herein decreases at a human body temperature;

(v) A process of the present invention overcomes the conventional problems such as the use of organic solvent, complicated preparation steps, a relatively high manufacture cost and a low loading efficiency; and (vi) A process of the present invention can ensure the stability of drugs without necessitating high-speed homogenization or ultrasonification generally carried out in the conventional process.

EXAMPLES

The following examples illustrate the invention and are not intended to limit the same.

Experimental

Materials

Pluronic F-127 (E100P65E100, MW12,600) (PF 127) was a kind donation from BASF Corp. (Seoul, Korea). Acryloyl chloride, triethylamine, and anhydrous toluene were obtained from Aldrich (Milwaukee, Wis., USA). 4-(2-Hydroxyethoxy)phenyl-(2-hydroxy-2-propyl) ketone (Irgacure 2959) was purchased from Ciba Specialty Chemicals Inc. (Basel, Switzerland). Potassium bromide, fluorescein isothiocyanate-labelled bovine serum albumin (FITC-BSA), potassium phosphate monobasic, sodium phosphate dibasic, and sodium azide were obtained from Sigma (St. Louis, Mo., USA). Sodium chloride and potassium chloride were purchased from Merck (Darmstadt, Germany). Nanosep™ centrifugal devices (MWCO 300,000) were obtained from Pall Life Sciences (Ann Arbor, Mich., USA), and dialysis membrane [cellulose ester (CE), MWCO 300,000 with a nomimal pore size of 35 nm] was the product of Spectrum (Houston, Tex., USA). Cellulose sterilization syringe filters (0.2 μm) were purchased from Whatman (Florham Park, N.J., USA).

Preparation of Pluronic-Based Nano-Carriers

Pluronic-based nano-carriers were prepared as schematically shown in FIG. 1. Hydroxyl groups of pluronic F-127 (PF 127) were acrylated by reacting 5 g of PF 127 and a 10-fold molar excess of both acryloyl chloride and triethylamine in 50 mL anhydrous toluene, which was allowed to stir under argon overnight. The obtained polymer was precipitated in anhydrous diethyl ether, filtered, and dried under vacuum for 3 days. The degree of acrylation was over 98%, as determined by 300 MHz $^1$H-NMR spectroscopy (JNM-LA300WB FT-NMR Spectrometer, JEOL, Japan).

DA-PF 127 was dissolved in de-ionized water to give 10% (w/w) precursor solution. This solution was then diluted with de-ionized water to make DA-PF 127 solutions with various concentrations (1.4, 0.77, 0.50, 0.33, and 0.20 wt %). A photoinitiator (Irgacure 2959) solution dissolved in 70% (v/v) ethanol was added to the diluted DA-PF 127 solution to make a 0.05 wt % initiator concentration. Then, the solution was UV-irradiated for 5, 10, or 15 min with 1.3 mW cm$^2$ intensity using an unfiltered UV lamp (VL-4.LC, 8 W, Vilber Lourmat, France) to give pluronic-based nano-carriers. Finally, the unreacted precursors were removed by spin filtration (14,000 rpm, 10 min) using Nanosep™ centrifugal devices, and the obtained pluronic-based nano-carriers were redispsered in distilled water.

Measurement of Critical Micelle Concentration

The critical micelle concentration (CMC) of DA-PF 127 was determined using pyrene as a fluorescence probe (K. C. Cho, et al., *Macromol. Res.*, 2006, 14, 348). Pyrene (Aldrich, Milwaukee, Wis., USA) dissolved in acetone was added to de-ionized water to give a concentration of $6 \times 10^{-6}$ M, and then acetone was removed through vacuum drying for 5 h. The concentration of DA-PF 127 was varied from 0.0001 to 1 wt % and incubated with pyrene solution (final concentration: $6 \times 10^{-7}$ M). A mixture of the DA-PF 127 solution and the pyrene solution was incubated at room temperature for 30 min in a dark condition. Fluorescence spectra were measured using a spectrofluorophotometer (Shimadzu, RF-5301PC, Kyoto, Japan) at an excitation wavelength of 339 nm and an emission wavelength of 390 nm.

Characterization of Pluronic-Based Nano-Carriers

The hydrodynamic diameter and the surface charge of pluronic-based nano-carriers were measured using an electrophoretic light scattering spectrophotometer equipped with a 10 mW He—Ne laser (632.8 nm) (ELS-8000, Otsuka Electronics Co., Japan) at a 90° scattering angle to the samples. Temperature was controlled, and the measurements were done in triplicate. Also, the thermo-reversible behavior of nano-carriers during temperature cycling was analyzed by repeatedly cycling between 20 and 37° C.

A transmission electron microscope (JEM-2100, JEOL, Japan) operating at 200 kV accelerating voltage was also used to get the image of the pluronic-based nano-carriers. TEM samples were prepared by drop-drying 20 μL of the pluronic-based nano-carrier suspension (0.77 wt % with 15 min UV-irradiation) pre-equilibrated at 4, 25, or 37° C. onto a 200-mesh carbon-coated copper grid at room temperature. The average diameter of the pluronic-based nano-carriers was determined by counting at least 50 nano-carriers in the TEM images. Gold nanoparticle (5 nm)-loaded nano-carriers were also prepared by co-incubating gold nanoparticles and nano-carriers at 4° C., and TEM images were obtained.

An FT-IR spectrometer (SPECTRUM 2000, Perkin-Elmer, USA) was used to evaluate the degree of photo-crosslinking of the pluronic-based nano-carriers. The pluronic-based nano-carriers (prepared from 0.77 wt % with 15 min UV-irradiation) were lyophilized and powdered by grinding, and mounted into a thin KBr film. IR spectra were obtained at a resolution of 1 cm$^{-1}$ with 20 scans in the wavenumber range from 4000 to 400 cm$^{-1}$. The double bonds remaining in the pluronic-based nano-carriers after photo-crosslinking were characterized by the IR peaks at around 1635 cm$^{-1}$ (C=C stretching of the double bonds).

Preparation and Characterization of Pluronic-Based Nano-Carriers Loaded with a Model Protein The pluronic-based nano-carrier (0.77 wt % with 15 min UV-irradiation) was loaded with a model protein, FITC-BSA (fluorescein isothiocyanate-labelled bovine serum albumin). The pluronic-based nano-carrier solution (1 mL) was added with 200 μg of FITC-BSA, and then incubated at 4° C. for 12 h to induce spontaneous loading of the protein inside the nano-carriers. Remaining model proteins were removed by spin filtration at room temperature.

The FITC-BSA encapsulation efficiency and the loading amount of the pluronic-based nano-carriers were determined by spin filtration at 14,000 rpm for 10 min at room temperature, and calculated as described in F. Q. Li, et al., *Int. J. Pharm.*, 2008, 349, 274. Then, FITC-BSA loaded pluronic-based nano-carriers were visualized using an inverted fluorescence microscope (TE2000-U, Nikon, Melville, N.Y., USA).

For FITC-BSA release from the pluronic-based nano-carriers, an FITC-BSA loaded nano-carrier suspension (0.5 mL) was put into a dialysis membrane tube. The tube was placed in 5 mL phosphate buffered saline (PBS) with 0.05% NaN$_3$ and kept in a shaking rocker at 30 rpm at 37° C. or 4° C. to characterize release pattern at a given temperature. The whole release medium was replaced with the fresh one at each time point. The amount of released FITC-BSA at each time point was analyzed using a Coomassie Plus-BradfordT™ assay (PIERCE, Rockford, Ill., USA). All measurements were performed in triplicate.

Preparation and Characterization of Pluronic-Based Nano-Carriers Loaded with Gold Nanoparticles The pluronic-based nano-carrier (0.77 wt % with 15 min UV-irradiation) was loaded with gold nanoparticles. The pluronic-based nano-carrier solution (1 mL) was mixed with 0.5 mL gold colloid (5 and 10 nm in size, Sigma, St. Louis, Mo., USA) solutions respectively, and then incubated at 4° C. for 12 h. To remove the unloaded gold nanoparticles, spin filtration was performed at 14,000 rpm for 10 min at room temperature. The release of gold nano-particles with different sizes was done similarly to the case of BSA release, and the amount of released gold nanoparticles at each time point was analyzed optically using a Cary 1E UV-visible spectrophotometer (Varian, Melbourne, Australia). All measurements were performed in triplicate.

Preparation and Characterization of Pluronic-Based Nano-Carriers Loaded with Gold Nanoparticles (NC-PF 68)

Figure 9:
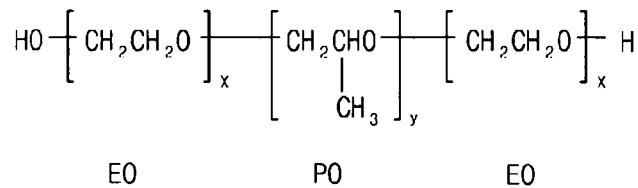
FIG. 9 shows the structure of pluronic block copolymers and structural properties of pluronic F-127 (PF 127) and F-68 (PF 68).

Pluronic-based nano-carriers were prepared by using pluronic F-68 (PF 68) among various pluronic block copolymers approved by FDA. Structural properties of PF 68 are shown in FIG. 9.

Diacrylated pluronic F-68 (DA-PF 68) with the degree of acrylation of 98% or higher was prepared as described above by using pluronic F-68 (PF 68). DA-PF 68 was dissolved in de-ionized water to give 10% (w/w) precursor solution. This solution was then diluted with de-ionized water to make 0.50% (w/w) DA-PF 127 solution. Then, the solution was UV-irradiated under the aforementioned UV polymerization conditions (e.g., 0.05 wt % initiator concentration) for 15 min to give pluronic-based nano-carriers.

Figure 3:
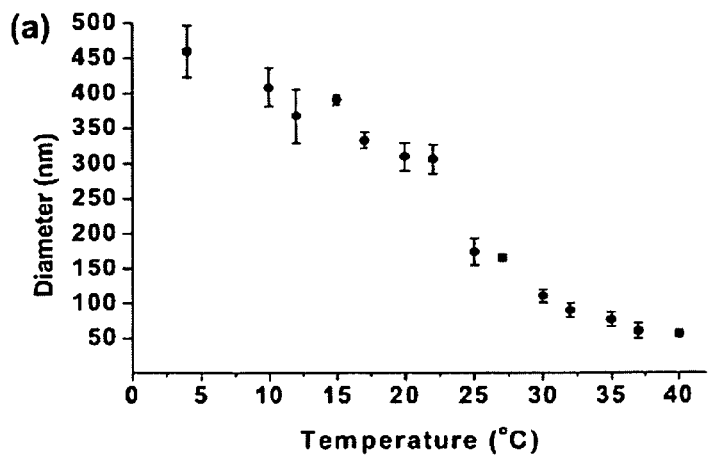
FIG. 3a shows the size change of the pluronic-based nano-carriers with temperature.
FIGS. 3b and 3c show the size distributions of nano-carriers when measured at 4° C. and 37° C.
Figure 3:
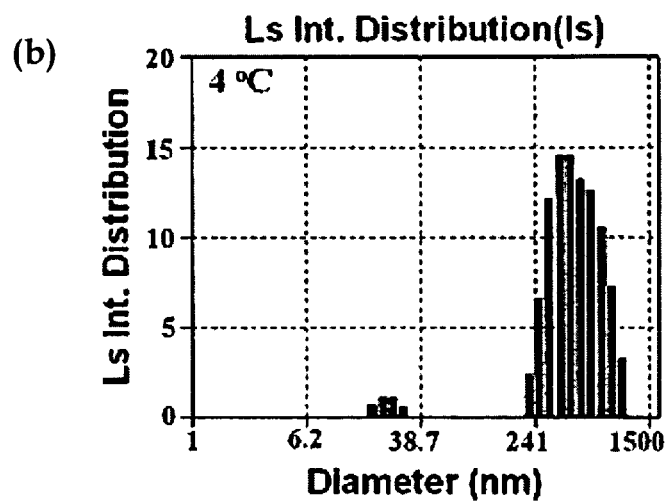
Figure 3:
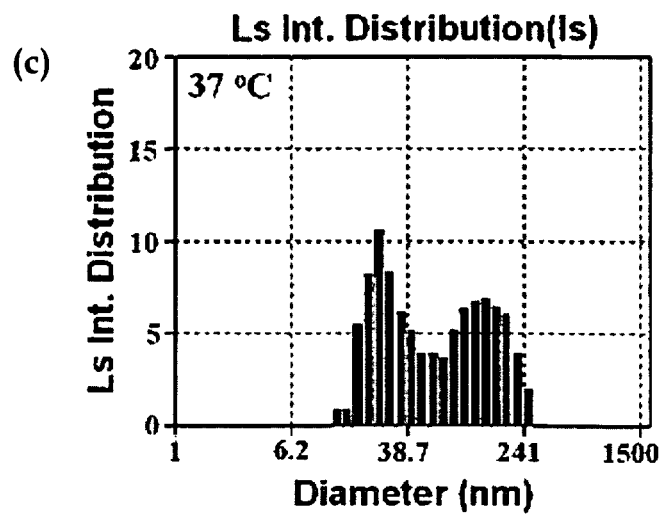

To ascertain the temperature-dependent properties of pluronic-based nano-carriers as shown in FIG. 3 (a), the average diameter of the pluronic-based nano-carriers was measured at various temperatures ranging from 4° C. to 40° C.

Preparation and Characterization of Pluronic-Based Nano-Carriers Loaded with Gold Nano-Rods Thus prepared 0.77% (w/w) pluronic-based nano-carriers (NC-PF 127) and 0.50% (w/w) pluronic-based nano-carriers (NC-PF 68), i.e. the pluronic-based nano-carriers (UV irradiation time: 15 min) were loaded with gold nano-rods. Pluronic-based nano-carriers solution (1 mL) and gold nano-rods (average size: 40 nm, aspect ratio: 3.9) 0.5 mL were mixed, and then incubated at 4° C. for 12 h to induce spontaneous loading of the gold nano-rods inside the nano-carriers. Unloaded gold nano-rods were removed by spin filtration at 10,000 rpm for 5 min. The pluronic-based nano-carriers loaded with gold nano-rods were redispsered in distilled water. Time-dependent change in absorbance spectra was analyzed by using 8453 UV-visible spectrophotometer (Agilent) at room temperature. All the measurements were carried out three times.

Results and Discussion

Formation of Pluronic-Based Nano-Carriers by Photo-Crosslinking

The aqueous solution containing only DA-PF 127 and initiator was photo-crosslinked at various conditions, and spin-filtered to remove the unreacted precursor polymers (DA-PF-127). As summarized in Table 1, this simple photo-crosslinking resulted in the formation of nano-size particles with relatively narrow size distribution for a certain concentration range. At a given initiator concentration (0.05 wt %) and a given UV-irradiation intensity (1.3 mWcm$^{-2}$), photo-crosslinked nano-carriers were obtained when the concentration ranged between 0.5 and 1.4 wt %. Above 2 wt %, big aggregates over micrometer size with a broad size distribution were observed, whereas photo-crosslinked nano-carriers were obtained after more than 15 min UV-irradiation for 0.33 wt % precursor concentration. No detectable nanoparticulates (over 30 nm) were observed at the same dynamic light scattering (DLS) set-up when the precursor concentration was below 0.2 wt %. In the precursor concentration range that could produce photo-crosslinked nano-carriers (from 0.33 to 1.4 wt %), the average diameter of these nano-carriers was increased gradually from 111±19 to 213±32 nm.

Figure 2:
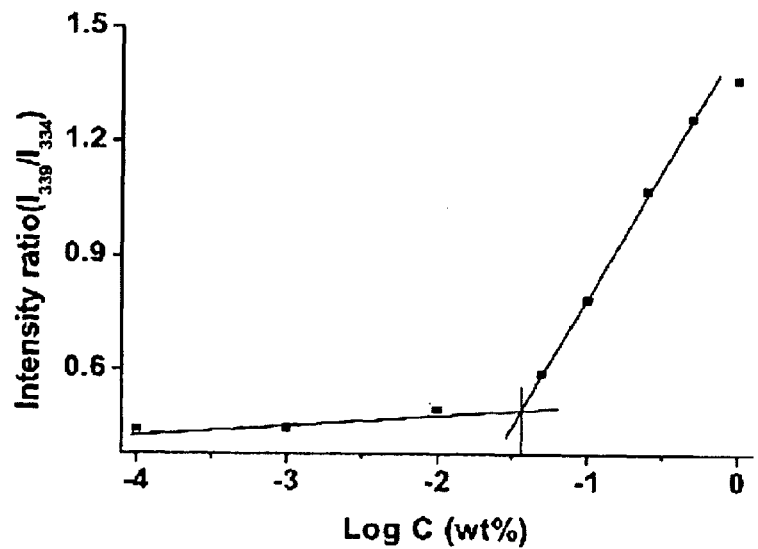
FIG. 2 shows the result of the determination of CMC (critical micelle concentration) of DA-PF 127 by using pyrene.

In contrast, for a given precursor concentration, the average size of photocrosslinked nano-carriers was not increased significantly by increasing the UV-irradiation time. Note that no particles over 30 nm in size was observed by the DLS set-up used before UV-irradiation at these concentrations. Thus, the nano-carriers obtained were formed by the photo-crosslinking of DA-PF 127. Also, these photo-crosslinked nano-carriers were not formed at lower concentrations than the critical micelle concentration (CMC, 0.038 wt %) of DA-PF 127 (FIG. 2). Therefore, it is apparent that the nano-carriers were formed by the photopolymerization among DA-PF 127 micelles (FIG. 1).

Table 1 shows size and polydispersity of the pluronic-based nano-carriers prepared at various conditions (UV intensity: 1.3 mW cm$^{-2}$), measured by DLS at 25° C. (mean±standard deviation with n=3).

TABLE 1

| DA-PF 127 Concentration (wt %) | UV-irradiation time (min) with 0.05 wt % initiator | | |
|---|---|---|---|
| | 5 | 10 | 15 |
| 2.0 | Aggregation | — | — |
| 1.4 | 209 ± 27 nm (0.25 ± 0.02) | 207 ± 18 nm (0.28 ± 0.04) | 213 ± 32 nm (0.26 ± 0.03) |
| 0.77 | 144 ± 17 nm (0.23 ± 0.02) | 149 ± 33 nm (0.22 ± 0.04) | 147 ± 21 nm (0.22 ± 0.03) |
| 0.50 | 113 ± 4 nm (0.22 ± 0.01) | 121 ± 11 nm (0.20 ± 0.03) | 135 ± 27 nm (0.24 ± 0.04) |
| 0.33 | x | x | 111 ± 19 nm (0.21 ± 0.01) |
| 0.20 | x | x | x |

Characterization of Pluronic-Based Nano-Carriers

Figure 4:
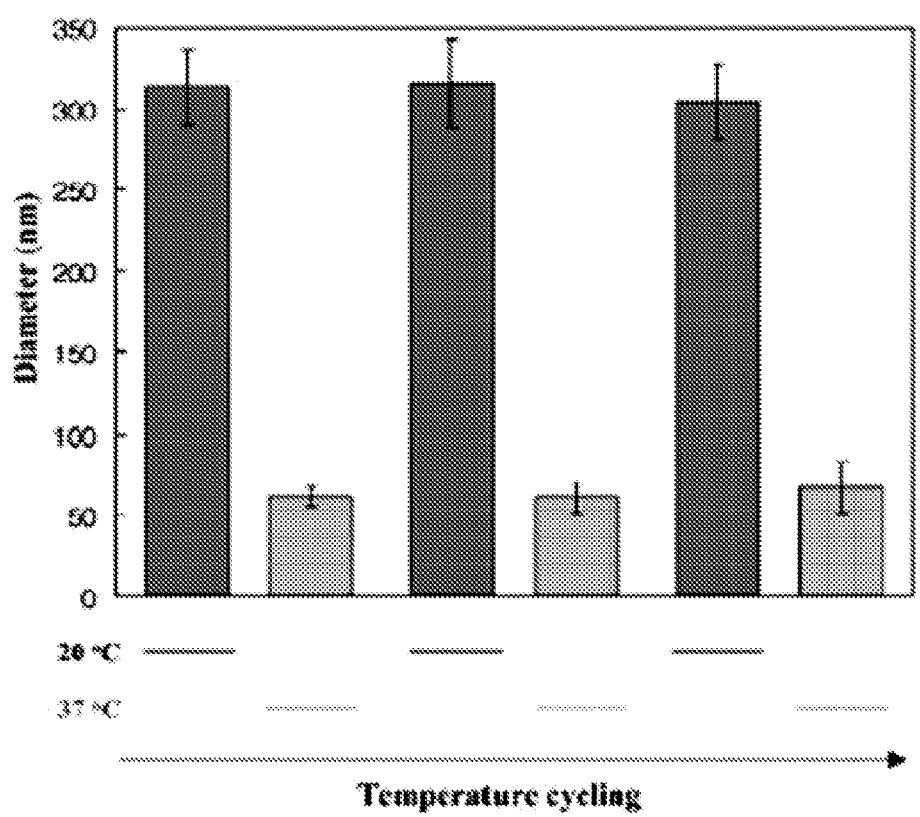
FIG. 4 shows a reversible size change of the nano-carrier with a temperature swing between 20° C. and 37° C., as measured by DLS.

As shown in FIG. 3 (a), the average diameter of the pluronic-based nano-carriers prepared from 0.77 wt % with 15 min of UV-irradiation was decreased from 460±37 nm to 55±5 nm by increasing the temperature from 4° C. to 40° C. Also, the size of pluronic-based nano-carriers prepared by the present method showed stable and relatively narrow distribution without any major aggregation at 4° C. and 37° C., respectively [FIGS. 3 (b) and (c)]. Reversible size change with a temperature swing between 20° C. and 37° C. (FIG. 4) also supports the stability of the nano-carriers.

Figure 5:
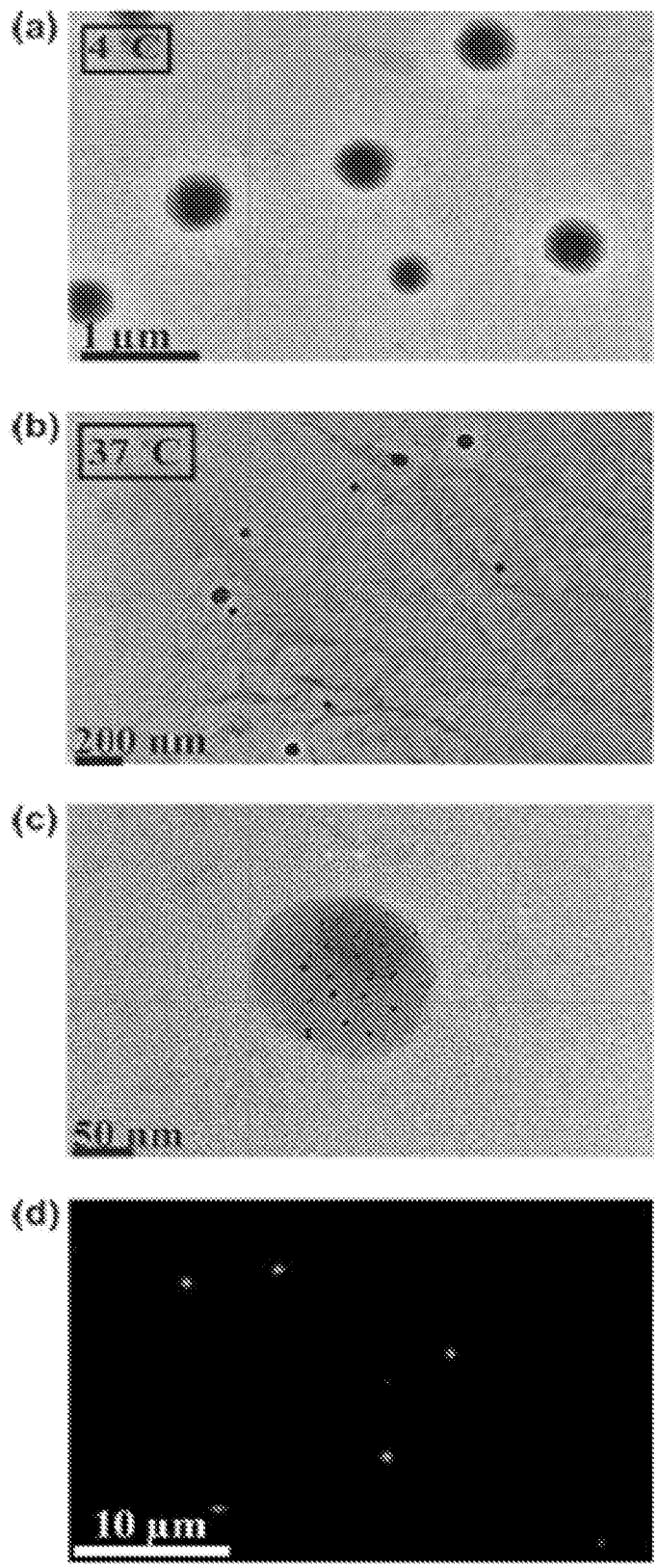
FIG. 5 show the images of the pluronic-based nano-carriers; TEM images of samples pre-equilibrated at (a) 4° C., (b) 37° C. and (c) after loading gold nanoparticle (5 nm); (d) Inverted fluorescence microscopy image of the FITC-BSA-loaded pluronic-based nano-carriers.

FIG. 5 is the TEM images of the pluronic-based nano-carriers prepared from 0.77 wt % with 15 min UV-irradiation, which indicate the presence of empty space in the nano-carriers. These images also show the round shape of the nano-carriers as well as the temperature-dependent change in size [FIGS. 5 (a) and (b)]. The average diameter of pluronic-based nano-carriers at room temperature was 160±20 nm, determined by counting more than 50 nano-carriers, which coincides well with the data from DLS (Table 1).

Figure 6:
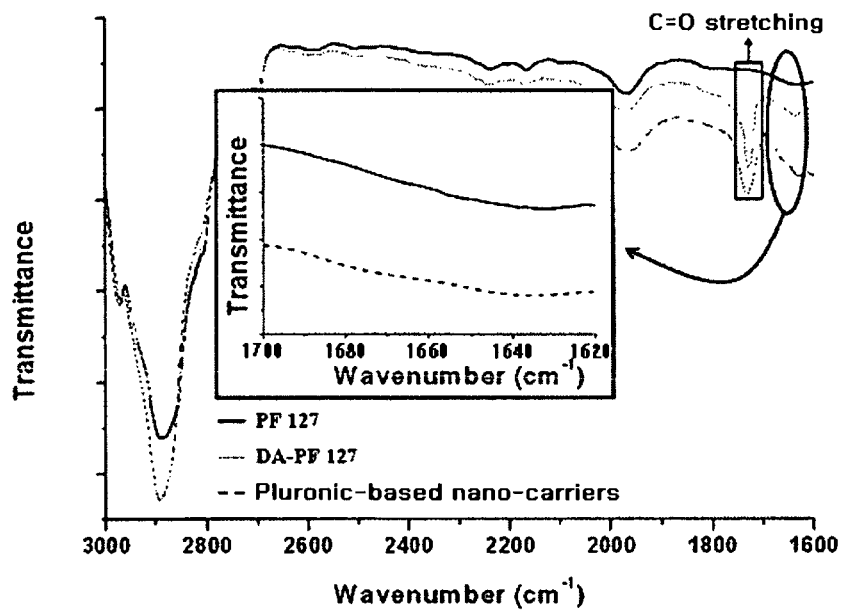
FIG. 6 shows the FT-IR spectra of pluronic F 127 (PF 127), diacrylated pluronic F 127 (DA-PF 127) and nano-carriers prepared by photo-crosslinking DA-PF 127, respectively.

The degree of conversion of acrylate groups (C=C double bond) of DA-PF 127 after photo-crosslinking was assayed using FT-IR spectroscopy. As shown in FIG. 6, the carbon-carbon double bond (C=C) of pluronic-based nano-carriers prepared from 0.77 wt % with 15 min UV-irradiation disappeared almost completely as compared with the IR peaks at around 1635 cm$^{-1}$ of original pluronic F 127 (PF 127) and DA-PF 127 without photo-crosslinking at the same concentration. This result indicates that the prepared pluronic-based nano-carriers were formed by the almost completely photopolymerized DA-PF 127, thus having a sufficient structural stability.

Figure 10:
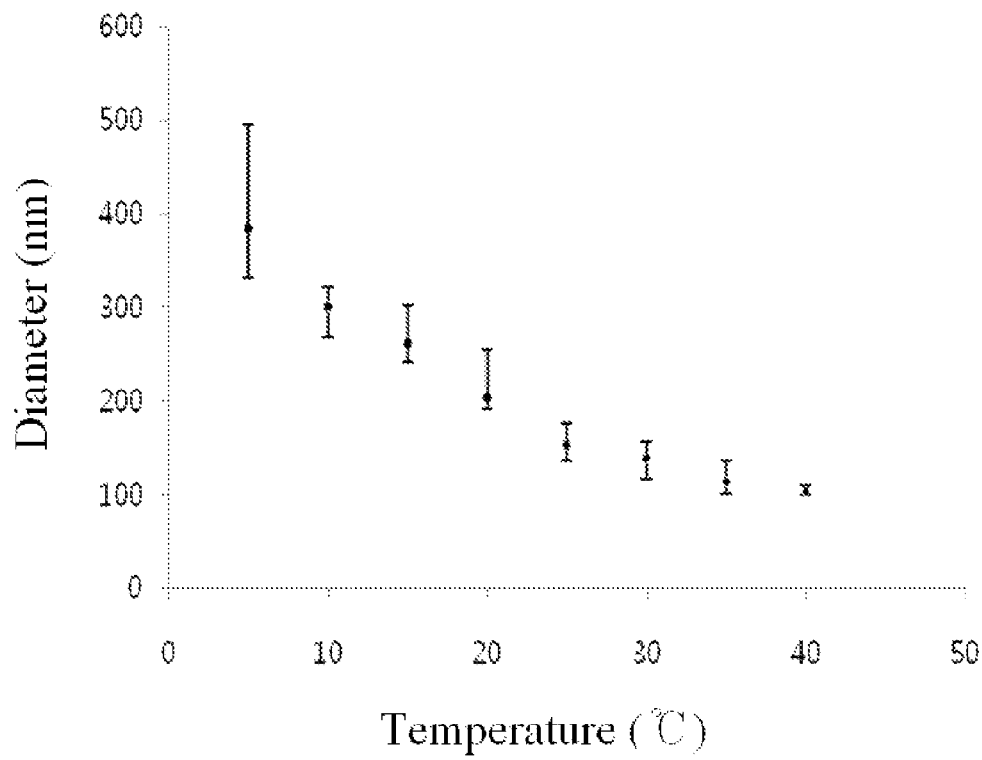
FIG. 10 shows the size change of 0.50% (w/w) pluronic-based nano-carriers (NC-PF 68) with temperature.

As shown in FIG. 10, the average diameter of 0.50% (w/w) pluronic-based nano-carriers (NC-PF 68, UV irradiation time: 15 min) was decreased from 384±51 nm to 99±5 nm as temperature increases from 4° C. to 40° C. Although this tendency is similar to that of 0.77% (w/w) pluronic-based nano-carriers (NC-PF 127, UV irradiation time: 15 min), NC-PF 68 is slightly larger than NC-PF 127 in size. This ascertains the possibility of controlling the size by using various raw materials.

Loading and Release of FITC-BSA and Gold Nanoparticles with Pluronic-Based Nano-Carriers FITC-conjugated BSA was selected as a model protein for the in vitro release experiments of the pluronic-based nano-carriers because the nano-carriers containing FITC-conjugated BSA could be apparently visualized by a fluorescence microscope. To load FITC-BSA into pluronic-based nano-carriers, the nano-carriers and FITC-BSA were simply incubated at 4° C. since the volume expansion of the nano-carriers at low temperature would lead to an open and porous layer structure of the nano-carriers. The average diameter and the size distribution of pluronic-based nano-carriers did not cause any noticeable changes after the incorporation of FITC-BSA. The encapsulation efficiency of FITC-BSA into the nano-carriers by this method was very high (>90%). FIG. 5 (d) shows the fluorescence microscopy images of FITC-BSA loaded pluronic-based nano-carriers, which indicates that FITC-BSA (MW 67,000) was well encapsulated inside the nano-carriers, confirmed by small green fluorescent dots.

Similarly, gold nanoparticles (with 5 and 10 nm in size) could be easily loaded by co-incubation with the nano-carrier at 4° C. TEM images of the gold nanoparticle-loaded nano-carrier revealed the entrapped gold nanoparticles inside the carrier [FIG. 5 (c)]. Combining the FITC-BSA loaded fluorescence image, gold nano-particle loaded TEM image, and the high loading capacity of the pluronic-based nano-carriers, it is apparent that the nano-carriers have the reservoir characteristics, thus can be used as carriers for target agents.

Figure 7:
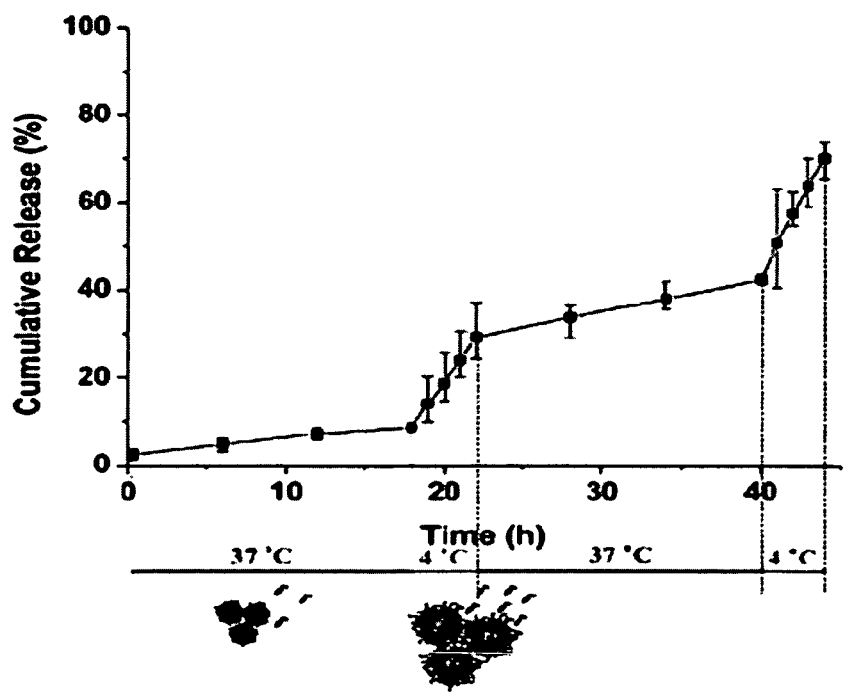
FIG. 7 shows the release pattern of FITC-BSA from the pluronic-based nano-carriers of the present invention under temperature modulation between 37° C. and 4° C.
Figure 8:
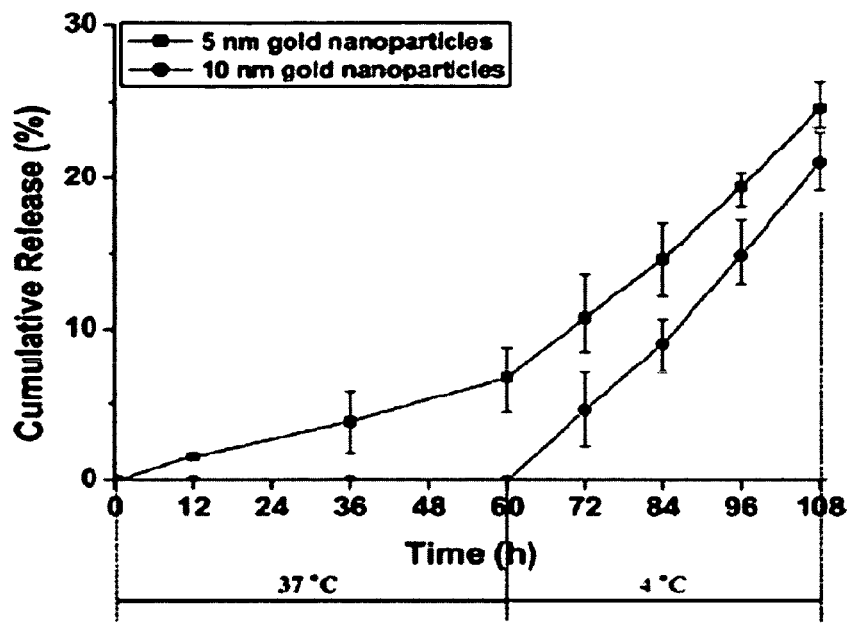
FIG. 8 shows the release of gold nanoparticles (5 and 10 nm in size) from the pluronic-based nano-carriers.

The release profile of FITC-BSA from the pluronic-based nano-carriers was characterized upon temperature modulation. As expected, the release rate was greatly reduced at 37° C. when the nano-carriers possess a packed layer structure, compared to 4° C. when the volume expansion of the nano-carriers induces an open and porous layer structure. This temperature-dependent release pattern (FIG. 7) was maintained repeatedly and reversibly. Also the protein release started at 37° C. with revealing the little initial burst. To get the pore size information of the nano-carriers, gold nanoparticles of 5 or 10 nm in size were loaded into the nano-carriers and the release profiles were obtained. Both of them were loaded into the nano-carriers at 4° C. with high efficiency (>90%). However, 5 nm gold particles were released slowly at 37° C., whereas no release was observed for 10 nm gold particles at 37° C. (FIG. 8). Thus, it can be estimated that the effective pore size of the nano-carriers at 37° C. is between 5 and 10 nm.

Loading Gold Nano-Rods and Evaluation of Nano-Rods in Pluronic-Based Nano-Carriers Gold nano-rods were easily loaded on nano-carriers of the present invention at 4° C. by a simple mixing like the afore-described model proteins.

Figure 11:
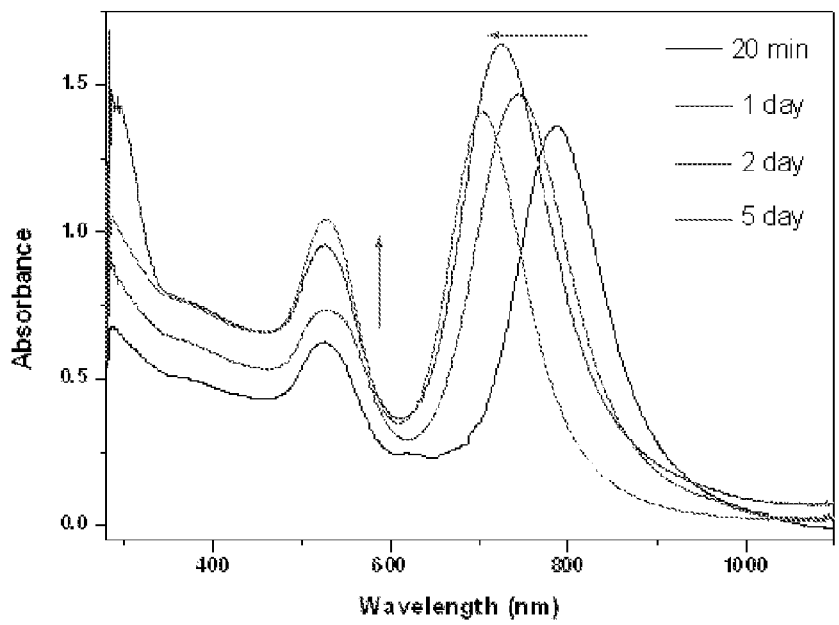
FIG. 11 shows the time-dependent absorbance spectra of gold nano-rods in aqueous solution.
Figure 12:
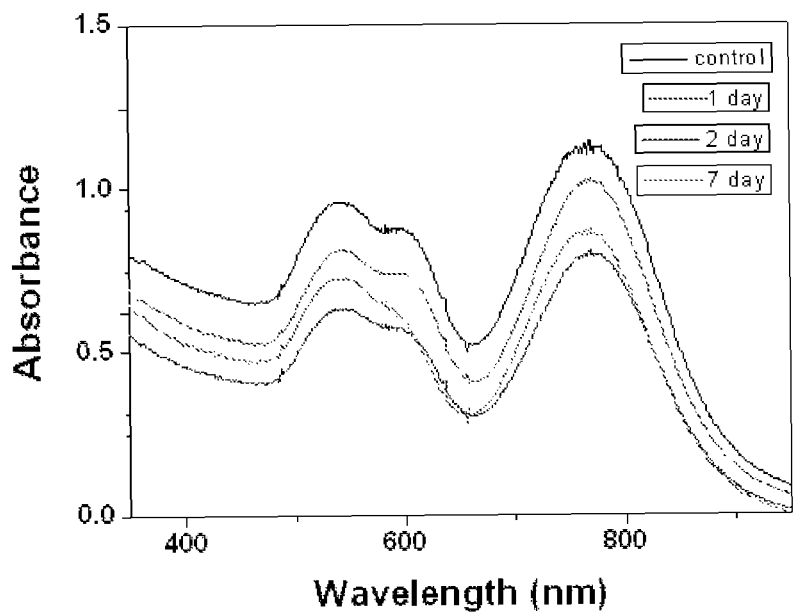
FIG. 12 shows the time-dependent absorbance spectra of gold nano-rods loaded on 0.77% (w/w) pluronic-based nano-carriers (NC-PF 127) in aqueous solution.
Figure 13:
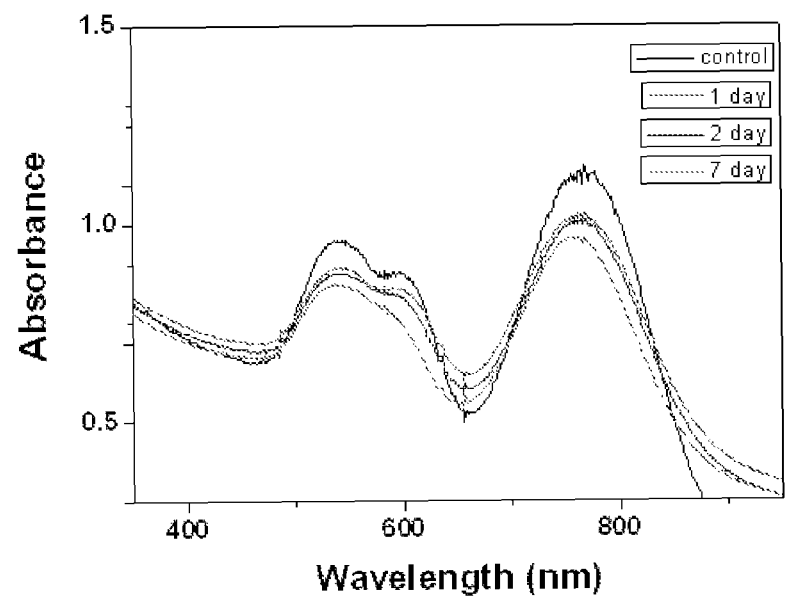
FIG. 13 shows the time-dependent absorbance spectra of gold nano-rods loaded on 0.50% (w/w) pluronic-based nano-carriers (NC-PF 68) in aqueous solution.

FIG. 11 shows that absorbance spectrum of gold nano-rods stored in aqueous solution drastically changes with time. In contrast, FIG. 12 and FIG. 13 show a long-term stability of gold nano-rods loaded on pluronic-based nano-carriers in aqueous solution. This ascertains that encapsulation of gold nano-rods in the present pluronic-based nano-carriers can enhance the stability of gold nano-rods, thus maintaining the optical absorption properties of them, which is a key parameter in biomedical application of gold nano-rods. This result demonstrates another useful application of the present invention system.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A temperature-sensitive nano-carrier comprising a water-soluble polymer crosslinked through a photo-crosslinkable functional group at the end of the polymer, wherein the temperature-sensitive nano-carrier has a nanoparticulate form and pores in which said nano-carrier is capable of encapsulating materials, wherein the average diameter of the polymer changes depending on temperature, wherein the diameter of the temperature-sensitive nano-carrier is between 50 and 500 nm, and wherein the pore size of the temperature-sensitive nano-carrier at 37° C. is between 3 and 20 nm, wherein the photo-crosslinkable functional group is at least one of coumarin, thymine or cinnamate, and the polymer has a nanoparticulate form.

2. The nano-carrier of claim 1, wherein the photo-crosslinkable functional group comprises C=C double bond(s).

3. The nano-carrier of claim 1, wherein the water-soluble polymer is one or more selected from the group consisting of poly(ethylene glycol), poly(ethylene oxide), poly(vinyl alcohol), poly(ethylene oxide)-poly(propylene oxide) block copolymer, alkylcellulose, hydroxyalkyl cellulose, heparin, hyaluronic acid, chitosan, dextran and alginate.

4. The nano-carrier of claim 3, wherein the water-soluble polymer is a polymer of Formula 1:

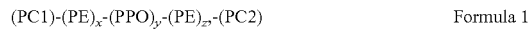

$(PC1)\text{-}(PE)_x\text{-}(PPO)_y\text{-}(PE)_z\text{-}(PC2)$   Formula 1 wherein PE is ethylene oxide; PPO is propylene oxide; each of PC1 and PC2 is a photo-crosslinkable functional group; and each of x, y and z is independently an integer of 1-10,000.

5. The nano-carrier of claim 1, wherein the average diameter of the temperature-sensitive nano-carrier increases as temperature decreases.

6. The nano-carrier of claim 1, wherein the nano-carrier is dispersed in an aqueous dispersion phase.

* * * * *